(12) United States Patent
Michels et al.

(10) Patent No.: US 8,608,727 B2
(45) Date of Patent: Dec. 17, 2013

(54) DELIVERY SYSTEM AND METHOD

(75) Inventors: Lester D. Michels, Eden Prairie, MN (US); William L. Beling, New Brighton, MN (US); Kristin Finberg, Minneapolis, MN (US); Ronald G. Travis, Spring Lake Park, MN (US)

(73) Assignee: Smiths Medical ASD, Inc., Rockland, MA (US)

( * ) Notice: Subject to any disclaimer, the term of this patent is extended or adjusted under 35 U.S.C. 154(b) by 2746 days.

(21) Appl. No.: 10/791,370

(22) Filed: Mar. 1, 2004

(65) Prior Publication Data
US 2005/0192559 A1 Sep. 1, 2005

(51) Int. Cl.
A61M 25/16 (2006.01)

(52) U.S. Cl.
USPC .................................. 604/533; 604/288.01

(58) Field of Classification Search
USPC ........... 604/533–539, 19, 93.01, 288.01, 523, 604/48
See application file for complete search history.

(56) References Cited

U.S. PATENT DOCUMENTS

| | | | |
|---|---|---|---|
| 3,851,646 A | 12/1974 | Sarns | |
| 4,013,310 A * | 3/1977 | Dye | 285/110 |
| 4,329,987 A | 5/1982 | Rogers et al. | |
| 4,453,289 A | 6/1984 | Kleykamp et al. | |
| 4,557,261 A | 12/1985 | Rügheimer | |
| 4,563,181 A | 1/1986 | Wijayarathna et al. | |
| 4,672,979 A | 6/1987 | Pohndorf | |
| 4,723,948 A | 2/1988 | Clark et al. | |
| 4,744,788 A | 5/1988 | Mercer, Jr. | |
| 4,826,477 A | 5/1989 | Adams | |
| 4,892,518 A | 1/1990 | Cupp et al. | |
| 4,895,570 A * | 1/1990 | Larkin | 604/411 |
| 4,898,591 A | 2/1990 | Jang et al. | |
| 5,053,015 A | 10/1991 | Gross | |
| 5,069,206 A | 12/1991 | Crosbie | |
| 5,129,891 A | 7/1992 | Young | |
| 5,135,502 A | 8/1992 | Koenig, Jr. et al. | |
| 5,152,747 A | 10/1992 | Olivier | |
| 5,171,227 A | 12/1992 | Twardowski et al. | |
| 5,178,612 A * | 1/1993 | Fenton, Jr. | 604/533 |
| 5,215,530 A | 6/1993 | Hogan | |
| 5,234,406 A | 8/1993 | Drasner et al. | |

(Continued)

FOREIGN PATENT DOCUMENTS

EP   0 537 892 A1   4/1993
EP   0 564 321 A2   10/1993

(Continued)

OTHER PUBLICATIONS

Abstract submitted to Society for Interventional Radiology in Oct. 2003, "In vivo evaluation of the microcatheter arterial port system for regional therapy" 1 page.

(Continued)

Primary Examiner — Emily Schmidt
Assistant Examiner — Michael J Anderson
(74) Attorney, Agent, or Firm — Louis Woo

(57) ABSTRACT

A connector and method of connecting are described for connecting a first and second catheter at an overlap area where the first catheter fits within the second catheter. The connector includes a collar that surrounds a portion of the overlap area and a clamp that applies a radially inward force to the collar and encircles a portion of the overlap area.

20 Claims, 13 Drawing Sheets

(56) References Cited

U.S. PATENT DOCUMENTS

| | | | |
|---|---|---|---|
| 5,344,414 A | | 9/1994 | Lopez et al. |
| 5,405,339 A | | 4/1995 | Kohnen et al. |
| 5,437,650 A | * | 8/1995 | Larkin et al. .................. 604/536 |
| 5,480,380 A | | 1/1996 | Martin |
| 5,527,278 A | | 6/1996 | Ensminger et al. |
| 5,531,695 A | | 7/1996 | Swisher |
| 5,556,381 A | | 9/1996 | Ensminger et al. |
| 5,558,641 A | * | 9/1996 | Glantz et al. ............. 604/288.02 |
| 5,599,325 A | | 2/1997 | Ju et al. |
| 5,637,102 A | * | 6/1997 | Tolkoff et al. ................ 604/536 |
| 5,683,403 A | | 11/1997 | Adams et al. |
| 5,725,513 A | | 3/1998 | Ju et al. |
| 5,762,636 A | | 6/1998 | Rupp et al. |
| 5,792,124 A | | 8/1998 | Horrigan et al. |
| 5,811,043 A | | 9/1998 | Horrigan et al. |
| 5,860,963 A | | 1/1999 | Azam et al. |
| 5,902,287 A | | 5/1999 | Martin |
| 5,911,715 A | | 6/1999 | Berg et al. |
| 5,931,801 A | | 8/1999 | Burbank et al. |
| 5,931,829 A | | 8/1999 | Burbank et al. |
| 5,938,653 A | | 8/1999 | Pepin |
| 5,941,823 A | | 8/1999 | Chait |
| 5,976,110 A | | 11/1999 | Greengrass et al. |
| 5,989,239 A | | 11/1999 | Finch et al. |
| 5,989,240 A | * | 11/1999 | Strowe ......................... 604/533 |
| 5,997,524 A | | 12/1999 | Burbank et al. |
| 6,007,516 A | | 12/1999 | Burbank et al. |
| 6,030,369 A | | 2/2000 | Engelson et al. |
| 6,090,099 A | | 7/2000 | Samson et al. |
| 6,099,519 A | | 8/2000 | Olsen et al. |
| 6,102,890 A | | 8/2000 | Stivland et al. |
| 6,113,572 A | * | 9/2000 | Gailey et al. ................ 604/93.01 |
| 6,120,492 A | | 9/2000 | Finch et al. |
| 6,143,013 A | | 11/2000 | Samson et al. |
| 6,146,325 A | * | 11/2000 | Lewis et al. ..................... 600/16 |
| 6,183,438 B1 | | 2/2001 | Berguer |
| 6,183,462 B1 | | 2/2001 | Beals |
| 6,193,684 B1 | | 2/2001 | Burbank et al. |
| 6,217,547 B1 | | 4/2001 | Lee |
| 6,238,369 B1 | | 5/2001 | Burbank et al. |
| 6,258,079 B1 | | 7/2001 | Burbank et al. |
| 6,261,255 B1 | | 7/2001 | Mullis et al. |
| 6,263,237 B1 | | 7/2001 | Rise |
| 6,368,316 B1 | | 4/2002 | Jansen et al. |
| 6,398,791 B1 | | 6/2002 | Que et al. |
| 6,464,684 B1 | | 10/2002 | Galdonik |
| 6,488,664 B1 | | 12/2002 | Solomon et al. |
| 6,508,807 B1 | * | 1/2003 | Peters ........................... 604/533 |
| 6,524,296 B1 | | 2/2003 | Beals |
| 6,562,022 B2 | | 5/2003 | Hoste et al. |
| 6,579,484 B1 | | 6/2003 | Tiernan et al. |
| 6,638,242 B2 | | 10/2003 | Wilson et al. |
| 6,663,614 B1 | | 12/2003 | Carter |
| 6,676,666 B2 | | 1/2004 | Vrba et al. |
| 6,685,720 B1 | | 2/2004 | Wu et al. |
| 6,796,586 B2 | * | 9/2004 | Werth ............................ 285/243 |
| 6,814,744 B2 | | 11/2004 | Yang et al. |
| 2002/0007158 A1 | | 1/2002 | Burbank et al. |
| 2003/0193190 A1 | * | 10/2003 | Werth ............................ 285/243 |

FOREIGN PATENT DOCUMENTS

| | | |
|---|---|---|
| WO | WO 92/13584 | 8/1992 |
| WO | WO 93/00129 | 1/1993 |
| WO | WO 98/31272 A2 | 7/1998 |
| WO | WO 98/31272 A3 | 7/1998 |

OTHER PUBLICATIONS

"FDA Premarket Notification Database Information for Port-A-Cath II Regional Arterial Portal System and Summary," http://www.accessdata.fda.gov, 2 pages and 7 pages (available at least as early as Feb. 27, 2004).

Waggershauser, T. et al., "Percutaneous Implantation of Port-Catheter Systems for Intra-Arterial Chemotherapy of the Liver," *Der Radiologe*, vol. 39, No. 9, pp. 772-776 (1999)—(English Translation included).

Kern, W. et al., "Phase I and pharmacokinetic study of hepatic arterial infusion with oxaliplatin in combination with folinic acid and 5-fluorouracil in patients with hepatic metastases from colorectal cancer," *Annals of Oncology*, vol. 12, pp. 599-603 (2001).

Cohen, A. et al., "Transbrachial Hepatic Arterial Chemotherapy Using an Implanted Infusion Pump," *Dis. Col. & Rect.*, vol. 23, No. 4, pp. 223-227 (May-Jun. 1980).

Cohen, A. et al., "Treatment of Hepatic Metastases by Transaxillary Hepatic Artery Chemotherapy Using an Implanted Drug Pump," *Cancer*, vol. 51, No. 11, pp. 2013-2019 (Jun. 1, 1983).

Ensminger, W. et al., "Totally Implanted Drug Delivery System for Hepatic Arterial Chemotherapy," *Cancer Treatment Reports*, vol. 65, No. 5-6, pp. 393-400 (May/Jun. 1981).

Fulton, Jr., R. et al., "In vitro and in vivo rates of fluid flow through catheters in peripheral veins of dogs," *JAVMA*, vol. 198, No. 9, pp. 1622-1624 (May 1, 1991).

Iserson, K. et al., "Combined Effect of Catheter and Tubing Size on Fluid Flow," *Am. J. Emerg. Med.*, vol. 4, No. 3, pp. 238-240 (May 1986).

* cited by examiner

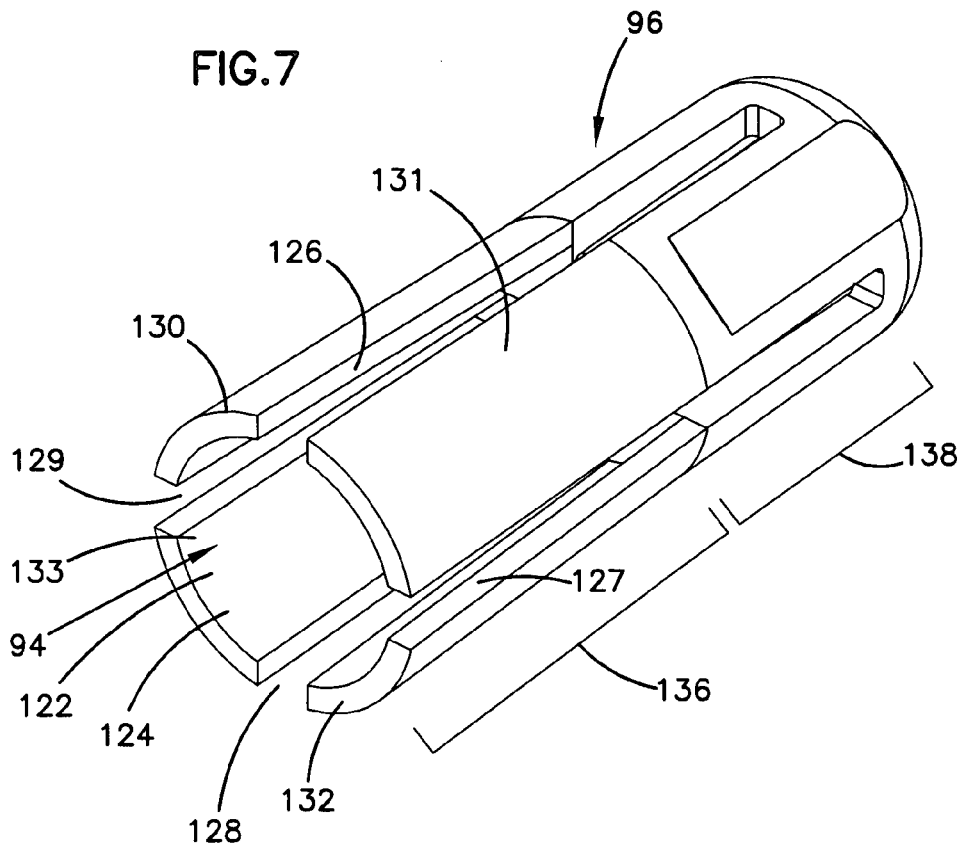
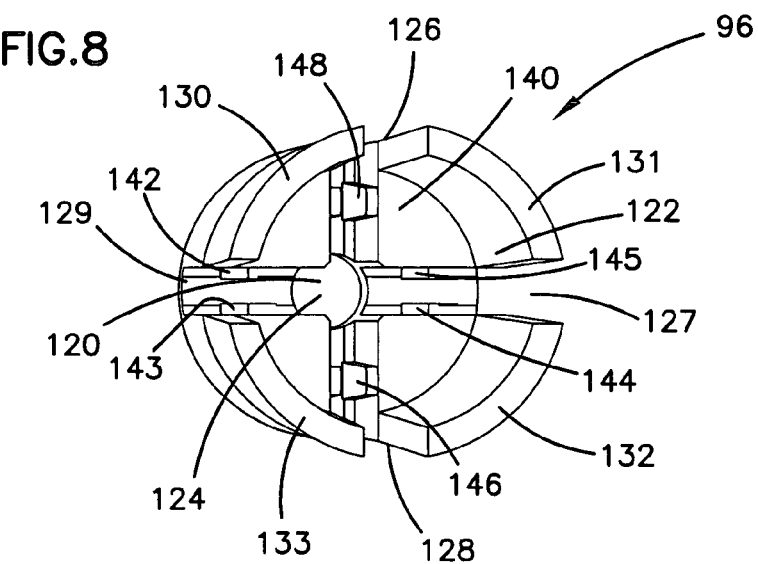

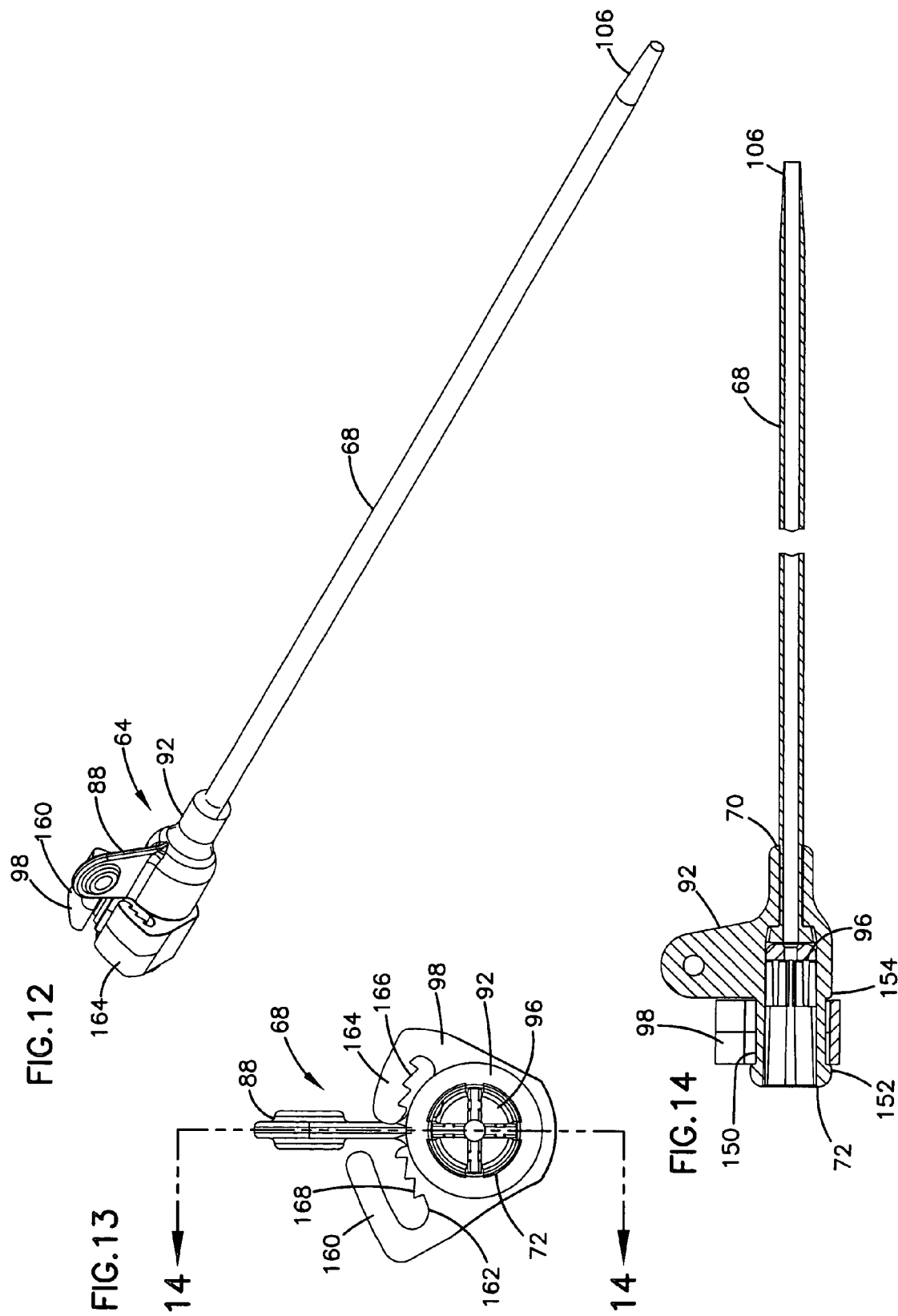

DELIVERY SYSTEM AND METHOD

FIELD OF THE INVENTION

The present invention is directed to a method and system for delivering a fluid to an area of a body, for example, for delivering a fluid containing an active agent. One possible application of the invention is the delivery of chemotherapy or other disease treatments to a body area, such as the liver.

BACKGROUND OF THE INVENTION

Many different drug deliveries systems are known for delivering a fluid or an active agent to a body. Some systems are designed to deliver active agents to a certain region of a body. For example, regional chemotherapy has been used in place of systemic chemotherapy, particularly in the context of liver metastases of colorectal cancer.

One system designed for chemotherapy of a target organ, such as the liver, is discussed in two articles: Karin Anna Herrmann, M D et al. *Liver Intra-arterial Chemotherapy: Use of the Femoral Artery for Percutaneous Implantation of Catheter-Port Systems*, RADIOLOGY, April 2000 at. 294 and T. Waggenhauser et al., *Perkutane Implantation von Portsysteme in der Arteria hepatica*, DER RADIOLOGE September 1999 at 772. This system includes an implantable port, a silicone catheter connected to the implantable port and an angiographic catheter connected to the silicone catheter by a metal cannula. One portion of the metal cannula fits within the proximal end of the angiographic catheter while the remainder of the metal cannula fits within the distal end of the silicone catheter. Sutures are used to secure the ends of the angiographic and silicone catheters together around the metal cannula.

Improved catheter-port systems are needed for easier assembly and use during the implantation process. In addition, improved connectors for connecting two catheters are desired. Further, systems that facilitate the healing of a wound in a vessel wall at the entry point of a drug delivery catheter are desired.

SUMMARY OF THE INVENTION

A system is described for implantation into a body to deliver fluid to a location within the body. The system includes a first catheter and a second catheter, where one end of the first catheter can be received within one end of the second catheter. When the first and second catheters are connected, the second catheter receives the first catheter along an overlap area. The system also includes a collar with a first opening configured to encircle the first catheter and a second opening configured to encircle the second catheter. The first opening is smaller than the second opening. The collar is configured to surround at least a first portion of the overlap area of the first and second catheters. The system also includes a clamp for applying a radially inward force to the collar to hold the first and second catheters together, where the clamp encircles at least a portion of the overlap area.

Another embodiment of the invention is a connector for connecting a first catheter and a second catheter where one end of the first catheter is configured to be received within one end of the second catheter. The collar has a first opening configured to encircle the first catheter and a second opening configured to encircle the second catheter. The connector includes a clamp for applying a radially inward force to the collar.

Another embodiment of the invention is another connector for connecting a first catheter and a second catheter where the connector includes a collar, a clamp, and a sleeve encircled by the first opening of the collar and configured to surround the first catheter. The sleeve has an outer diameter larger than an inner diameter of the first catheter and the sleeve is configured to extend along the first catheter into an incision site.

In another embodiment of the invention, a connector includes a collar, a clamp and the collar defines a cavity adjacent to the second opening and encircled by the clamp. The connector further includes a collet within this cavity where the collet is configured to surround at least the first portion of the overlap area of the first and second catheters. The collet is more rigid than both the first and second catheters.

Another embodiment of the present invention is a method of connecting a first catheter and a second catheter. The first catheter is positioned within a body lumen through an incision site in the body lumen. The connector is moved relative to the first catheter so that a sleeve of the connector enters the incision site. Next, a proximal end of the first catheter is cut near where the first catheter emerges from the second opening of the connector. The second catheter is slid over the cut end of the first catheter and into the cavity of the connector. Then the clamp of the connector is closed to apply a radially inward force to the overlap area of the first and second catheter.

BRIEF DESCRIPTION OF THE DRAWINGS

The invention may be more completely understood by considering the detailed description of the various embodiments of the invention that follows in connection with the accompanying drawings.

FIG. 7 is a perspective view of a collet which is a component of the connector of FIG. 6.

FIG. 8 is a perspective end view of the collet of FIG. 7.

FIG. 12 is a perspective view of one embodiment of a connector for a delivery system of the present invention.

FIG. 13 is an end view of the connector of FIG. 12.

FIG. 14 is a cross-sectional view of the connector of FIG. 12 taken along line 14-14 in FIG. 13.

Figure 1:
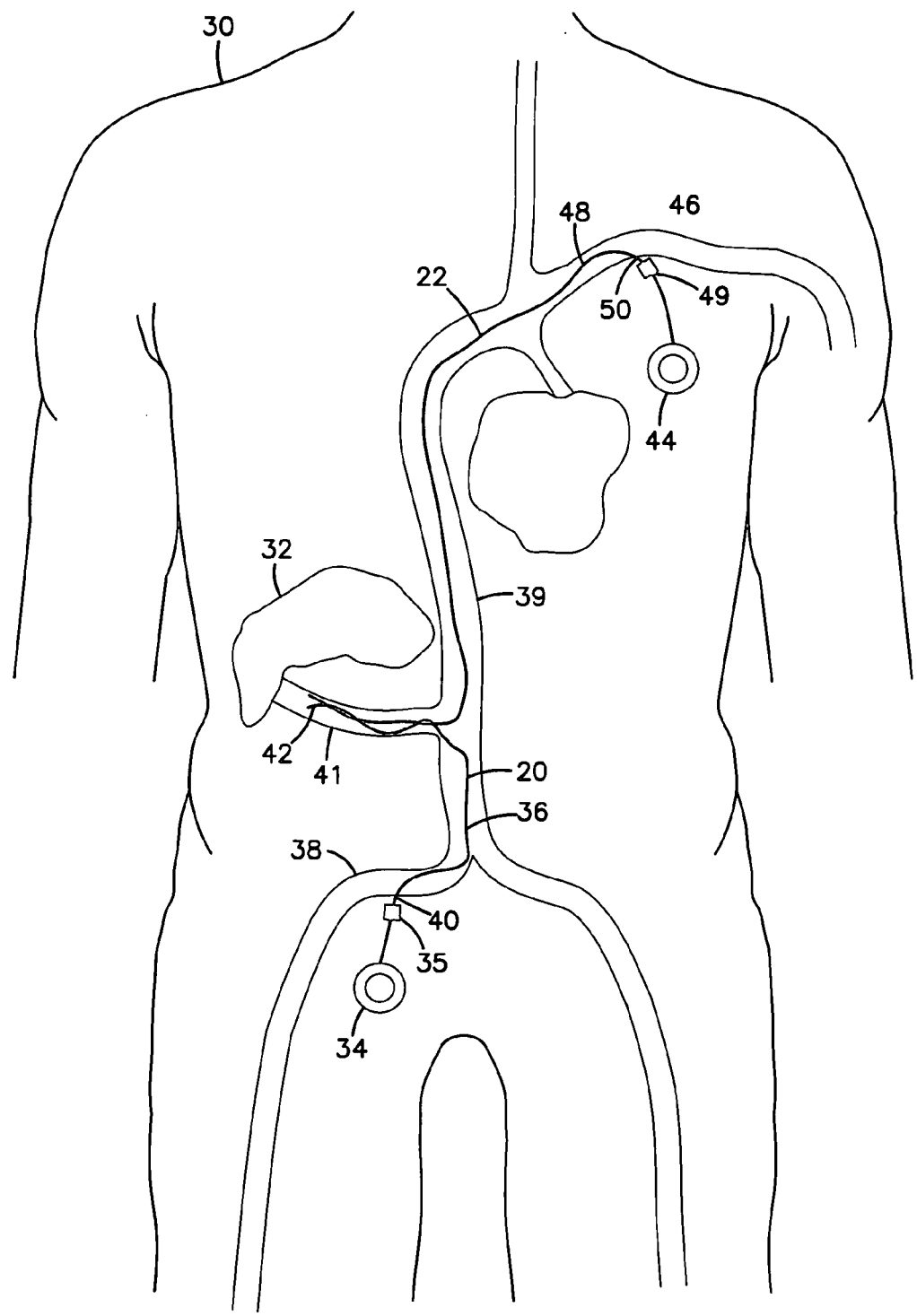
FIG. 1 is a schematic drawing of a human body showing two possible locations for percutaneous implantation of a delivery system according to the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION OF THE VARIOUS EMBODIMENTS

The present invention is believed to be applicable to a variety of systems and methods for delivering a fluid, such as an active agent or a drug, to an area of a body. The invention has been found to be particularly advantageous in delivering a drug treatment course to an area of a body. While the present invention is not so limited, and could be used for the delivery or removal of many different kinds of fluids, an appreciation of the various aspects of the invention is best gained through a discussion of the application examples operating in the disease treatment environment.

FIG. 1 illustrates one particular embodiment of a delivery system of the present invention positioned within a body. This embodiment of the delivery system is particularly well suited to deliver fluids to specific organs of the body via the vascular system that directly supplies these organs. The delivery system of this embodiment includes an implantable access device with a resealable septum for receiving injections of fluid. A length of catheter or tubing is connected to the access device at one end, tunneled subcutaneously so that the other end is near an incision site into an artery, and connected to a fluid delivery catheter at that end. The delivery catheter is positioned within the vascular system so that its delivery tip is located at the point in or near the organ where fluid delivery is desired. Two different delivery systems 20, 22 are illustrated implanted into a body 30 in two different locations in FIG. 1. Both systems 20, 22 are positioned to deliver an agent to the liver 32. The first system 20 includes an access device 34 positioned in the groin area. The access device is connected via a length of tubing to a delivery catheter 36 by a connector 35. The catheter 36 enters the femoral artery 38 at an incision site 40 into the femoral artery 38. The catheter 36 travels through the aorta 39 and then the hepatic artery 41. The delivery tip 42 of the catheter 36 is positioned near the liver 32 in the vasculature supplying the liver.

A second system 22 is shown positioned in an alternate location in the body. An access device 44 is positioned near the subclavian or brachial artery 46. A tubing is connected to the access device 44 and also connected to a catheter 48 by a connector 49. The catheter 48 enters the subclavian artery 46 at an incision site 50. From the incision site 50, the catheter travels through the aorta 39 to the hepatic artery 41 near the liver. The two placement locations illustrated in FIG. 1 are two examples of the possible location of system components for delivery to the liver. Specific patient anatomy and physician judgment will be considered in implanting the system in a particular patient. Many different placement locations may be utilized for drug delivery to different areas of the body.

Figure 2:
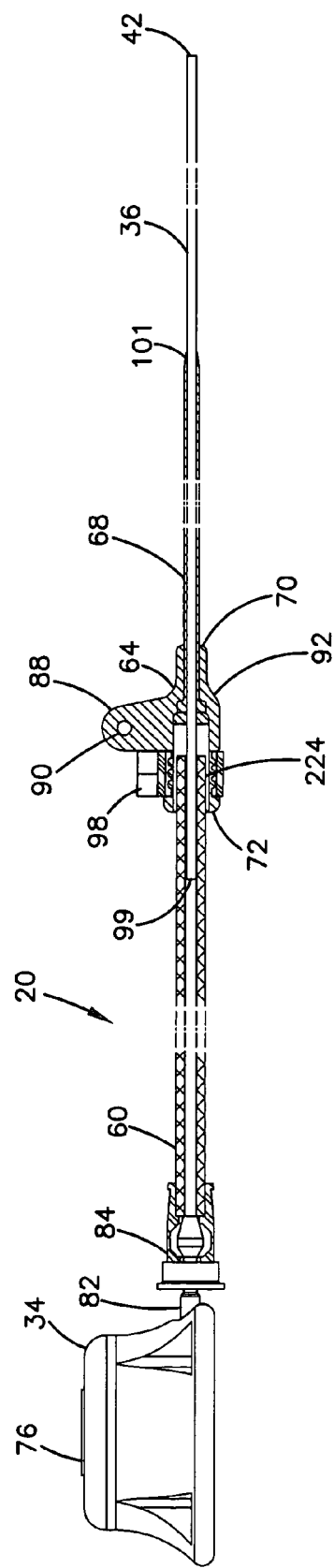
FIG. 2 is a side partial cross-section view of a delivery system according to the present invention.

The components of the delivery system 20 are shown in more detail in FIG. 2, including the access device 34 and the delivery catheter 36. The system 20 also includes a second catheter or section of tubing 60 and a connector 64 for connecting the tubing 60 with the delivery catheter 36. The connector 64 includes a sleeve 68 extending from a first opening 70 of the connector along a section of the delivery catheter 36. The connector 64 includes a second opening 72 in which the tubing 60 is received. For ease of illustration, the tubing 60, sleeve 68, and delivery catheter 36 are illustrated in an abbreviated manner with a section along their length removed, so that the entire length of these components is not shown in FIG. 2. The system 20 may be used to access a patient's vascular system where the distal tip of the delivery catheter 36 will be positioned in a tissue, such as an organ, with the intent to maintain this position for an extended period of time. For example, the tip of the delivery catheter 36 may be left in place for several days or several weeks. The term distal is used herein to convey being situated away from the point of entry of a system into the body, within the body, when the system is being implanted. The term proximal is used to convey being situated near to the point of entry into the body.

It is important that the tip of the delivery catheter stays in approximately the same position within the patient's vasculature during the time that it is implanted. However, patient movement may affect the tip location of the catheter. Some features of the delivery catheter may make it more likely that patient movement that affects the implanted port will be translated to movement of the delivery catheter tip. For example, the delivery catheter needs to be relatively stiff in order to have the pushability and torqueability required to move the catheter through the tortuous path through the patient's vasculature. The stiffness of the delivery catheter also makes it more likely that movement of the catheter along its length will result in a change in position of the tip of the delivery catheter.

In contrast, materials that are more flexible and have a greater percentage of elongation under stress would not be as likely to transmit movement to the tip. To address this issue, the tubing 60 is included in the system 20 between the delivery catheter 36 and the implanted port. The tubing 60 is made of a material that elongates under tension more than the delivery catheter material. As a result, the inclusion of the tubing 60 in the system 20 provides a strain relief function. If the patient's body movement results in movement of the implanted port 34, that movement is not necessarily translated along the length of the delivery catheter to its tip 42. Instead, the tubing 60 elongates in response and absorbs the movement of the port without translating that movement to the delivery catheter tip 42. As a result, the delivery catheter tip 42 is more likely to stay within a very short distance of its original position despite the body movement of the patient. For example, the delivery catheter tip 42 is likely to stay within about 1 cm of its original location despite the patient's movement of the portion of the body where the port 34 is implanted, in one embodiment of the invention.

Also, it is not uncommon for one portion or another of a delivery system to become infected, occluded or need to be replaced for some other reason. When there is a need to relocate or replace the delivery catheter or the access device, the system facilitates the removal and replacement of certain components without disturbing the remainder of the system. For example, the delivery catheter may be removed and repositioned or replaced without disturbing the access device and the tubing. In addition, the access device 34 and the tubing 60 may be removed and replaced without disturbing the delivery catheter 36.

Figure 3:
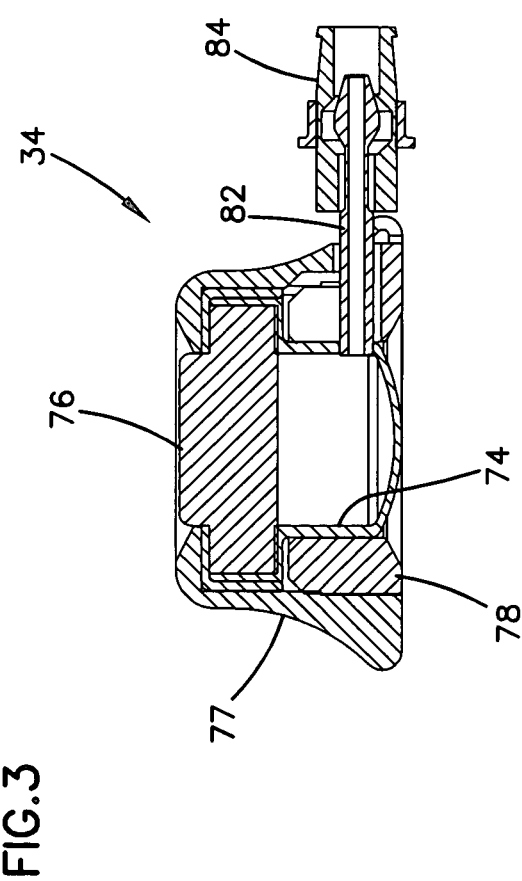
FIG. 3 is a cross-sectional view of a port included in the system of FIG. 2.

The access device 34 may be a needle penetrable chamber or lumen that is connectable to the tubing 60. The access device 34 provides an access point for the delivery of or withdrawal of fluid to or from vascular system 20. One embodiment of an access device or port that may be used with the present invention is illustrated in FIG. 3. The access device 34 may include a reservoir 74 sealed by a septum 76. The reservoir 74 is trapped between a top cover piece 77 and a base piece 78. The access device allows repeated puncture of the resealing septum 76. The outlet tube 82 allows for connection to the tubing 60. One mechanism for attaching the outlet tube 82 to the tubing 60 is the use of an access device sleeve 84. Many ports or other septum-sealed chambers may be used for the access device 34. For example, one of the PORT-A-CATH® II ports made by Smiths Medical MD, Inc. may be used. One example of a port that may be used with the system 20 is the port described in U.S. Pat. No. 5,558,641, the disclosure of which is hereby incorporated herein by reference. One port connection system is described in U.S. Pat. No. 4,703,948, the disclosure of which is hereby incorporated by reference.

The tubing 60 provides a fluid conduit between the access device 34 and the delivery catheter 36. In addition, the tubing 60 may serve the purpose of providing a strain relief component within the system. The access device is sutured to tissue under the skin of the patient. When the patient makes certain movements, the tip of the delivery catheter can be pulled back toward the access device. The tubing 60 may have a soft quality that allows for more stretching of the material than the delivery catheter 36. As a result, the movement of the patient will be less likely to cause significant dislocation of the delivery tip 42. To provide this strain relief function, the tubing 60 is softer than the delivery catheter 36 and is capable of more elongation when tension is applied. For example, the tubing 60 may be capable of elongating under stress at least about 50% of its length. In another embodiment, the tubing 60 is capable of elongating at least about 100% of its length. In yet another embodiment, the tubing 60 is capable of elongating at least about 200% of its length. The tubing segment may be made of many different materials, such as thermoplastic materials, thermal set materials, and rubber materials, such as silicones, polyurethanes, polyethylenes, polyvinyl chlorides and thermoplastic rubbers. The material of the tubing may have a durometer between 25 Shore A and 65 Shore A, in one embodiment. In one embodiment, the tubing 60 is made of silicone and has a durometer of about 45 Shore A. The tubing outer diameter may be less than about 5 mm, or more specifically, less than about 3 mm. In one embodiment, the outer diameter of the tubing is about 2.8 mm. The tubing inner diameter is sized so that it will receive the delivery catheter. The tubing inner diameter may be at least about 0.5 mm, or at least about 0.7 mm, or about 1 mm. In one embodiment, the walls of the tubing 60 will have a thickness of no greater than 4 mm or no greater than about 2 mm. In one embodiment, the walls of the tubing 60 will have a thickness of about 1.8 mm.

In one embodiment, the tubing walls are clear. This is desirable so that the catheter 36 may be viewed through the tubing wall in the overlap area 100. The tubing wall may include a stripe of radiopaque material so that can be easily located in the body.

The connector 64 joins the tubing 60 and the delivery catheter 36. The connector 64 provides a secure connection and seals the tubing 60 to the delivery catheter 36. As shown in the cross-sections of FIGS. 4 and 5, the connector 64 includes a first opening 70 that encircles the delivery catheter 36 and a second opening 72 that encircles the tubing 60. An overlap area 100 of the tubing 60 and catheter 36 is defined where the delivery catheter 36 fits within the tubing 60. A clamp 98 applies a radially inward force to a portion 102 of this overlap area.

The connector 64 includes a collar 92 that forms the base or foundation of the connector 64. The collar 92 supports or contacts the remainder of the connector components. The connector 64 surrounds a longer second portion 103 of the overlap area. The connector 64 also includes a suture tab 88 and a suture hole 90 to facilitate securing the connector to a specific tissue location within the body if desired.

If one part of the delivery system needs to be replaced, the connection between the tubing 60 and the delivery catheter 36 is severed by cutting the connector 64 out of the system. The tubing 60 is cut at a location proximal to the proximal end 99 of the delivery catheter 36, such as at a possible cut location 97. The delivery catheter 36 and connector may then be removed and replaced. Alternatively, the catheter may be cut to remove the connector 64 or the tubing 60 and the connector 64, while leaving the remainder of the catheter in place. Accordingly, the connector 64 along with portions of the tubing 60 and catheter 36 could be removed from a patient's body.

Other permanent connection mechanisms could be used in place of the connector 64. For example, the connector 64 could be replaced with solvent or adhesive chemical bonding, barbed fitments with or without crimp collars, extension tubes with swaged or crimped collars, connectors that are bondable to the outer diameter or inner diameter of a tubing, male/female connectors, bayonet and pin type connectors, or O-ring compression connectors. Many different junctions that are known in the art may be used in place of connector 64.

In an alternative embodiment, the connector allows for disconnection and reconnection of the system's key components, rather than requiring that the connector is cut out of the system. Instead, the delivery catheter 36 and tubing 60 may have connectable components at their ends to facilitate connection, disconnection and reconnection. Alternative re-attachable connectors include barbed female adapters with threaded or Luer lock connections, barbed male adapters with threaded or Luer lock connections, connectors with rotating or non-rotating lock rings, connectors that are bondable to the outer diameter or inner diameter of a tubing, bayonet and pin type connectors, or O-ring compression connectors with threaded connector components. The connector 64 illustrated in the Figures is a permanent connector that does not allow for disconnection and reconnection of the components. The connector 64 and its components will be illustrated in greater detail and discussed in relation to FIGS. 6-18.

The delivery catheter 36 is configured to be positioned within a patient's vasculature where delivery of a fluid is desired. Different patient applications will require different types of delivery catheter 36. Many different delivery catheters are known to those of skill in the art and may be used with the system. The specific construction of a delivery catheter 36 that may be used to deliver fluid to small vasculature within a patient, such as to the liver, will be described in detail with respect to FIG. 19.

Figure 4:
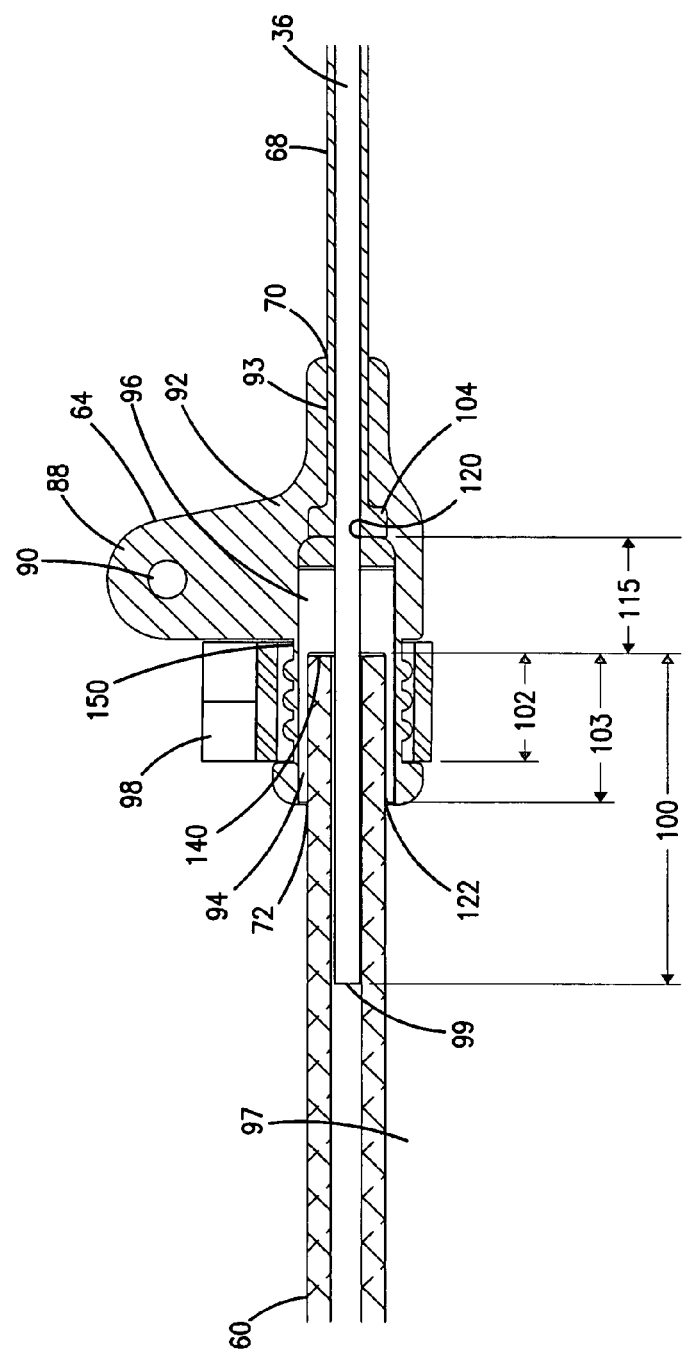
FIG. 4 is an enlarged cross-sectional view of a portion of the system of FIG. 2, including a connector.
Figure 5:
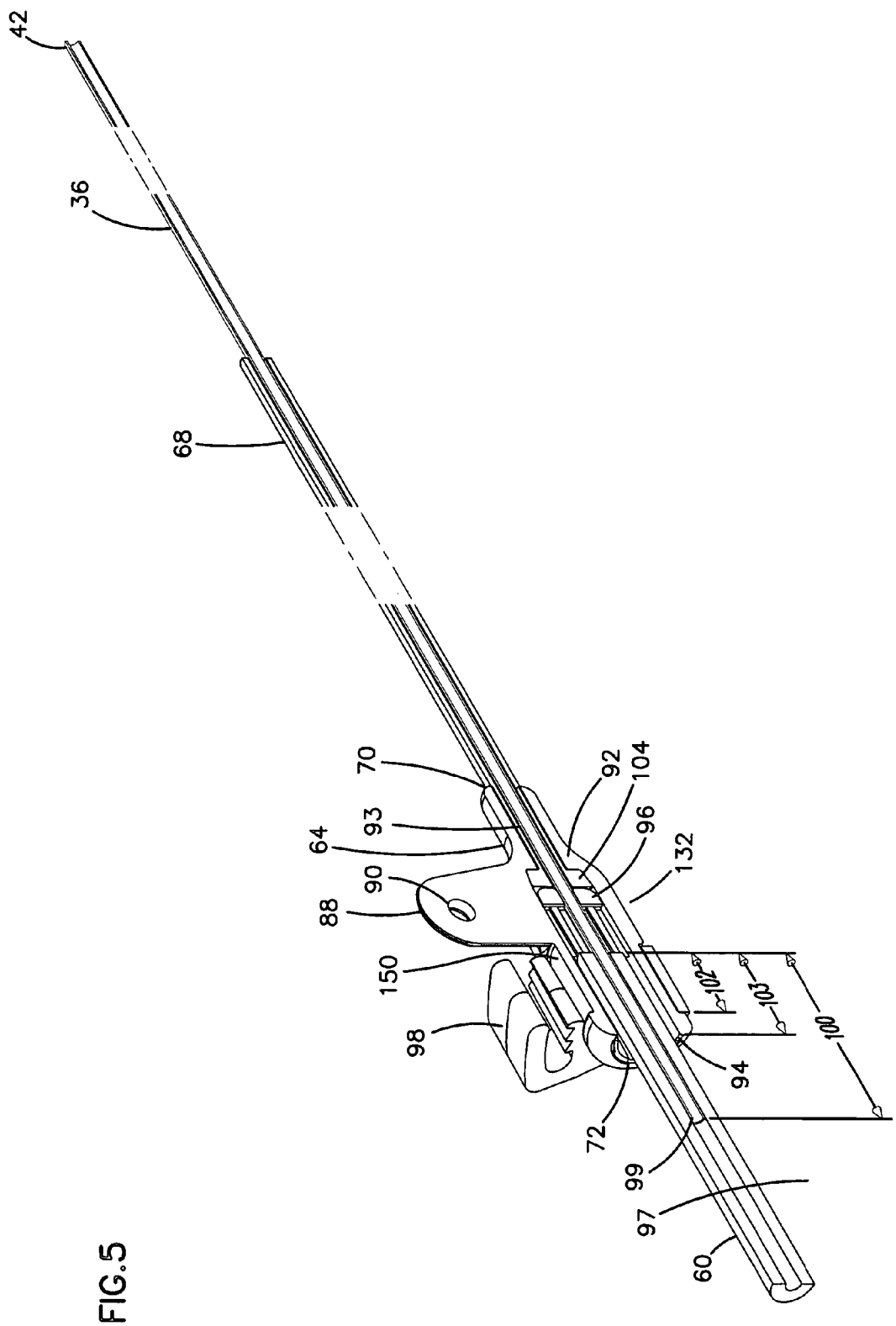
FIG. 5 is a cut-away cross-sectional view of a portion of a delivery system of the present invention including a connector.

FIGS. 4 and 5 show cross-sectional or cut-away views of the tubing 60 and delivery catheter 36 joined by the connector 64. The connector and its components are further illustrated in FIGS. 6-18. As illustrated in the exploded view of FIG. 6, the collar 92 defines a first cavity or chamber 93 and a second cavity or chamber 94. Both of these cavities are cylindrical cavities, and the diameter of the first cavity 93 is smaller than the diameter of the second cavity 94. When the connector is in use as shown in FIGS. 4-5, a portion of the catheter 36 lies within the first cavity 93. A portion of both the catheter 36 and the tubing 60 lie within the second cavity 94. A collet 96 also lies within the second cavity 94 and facilitates the action of a clamp 98 on the tubing 60 and the catheter 36. The collar 92 may be made of silicone or many other materials. In one embodiment, the durometer of the collar material is about 40-60 Shore A. In a particular embodiment, the durometer of the collar material is about 50 Shore A.

Figure 6:
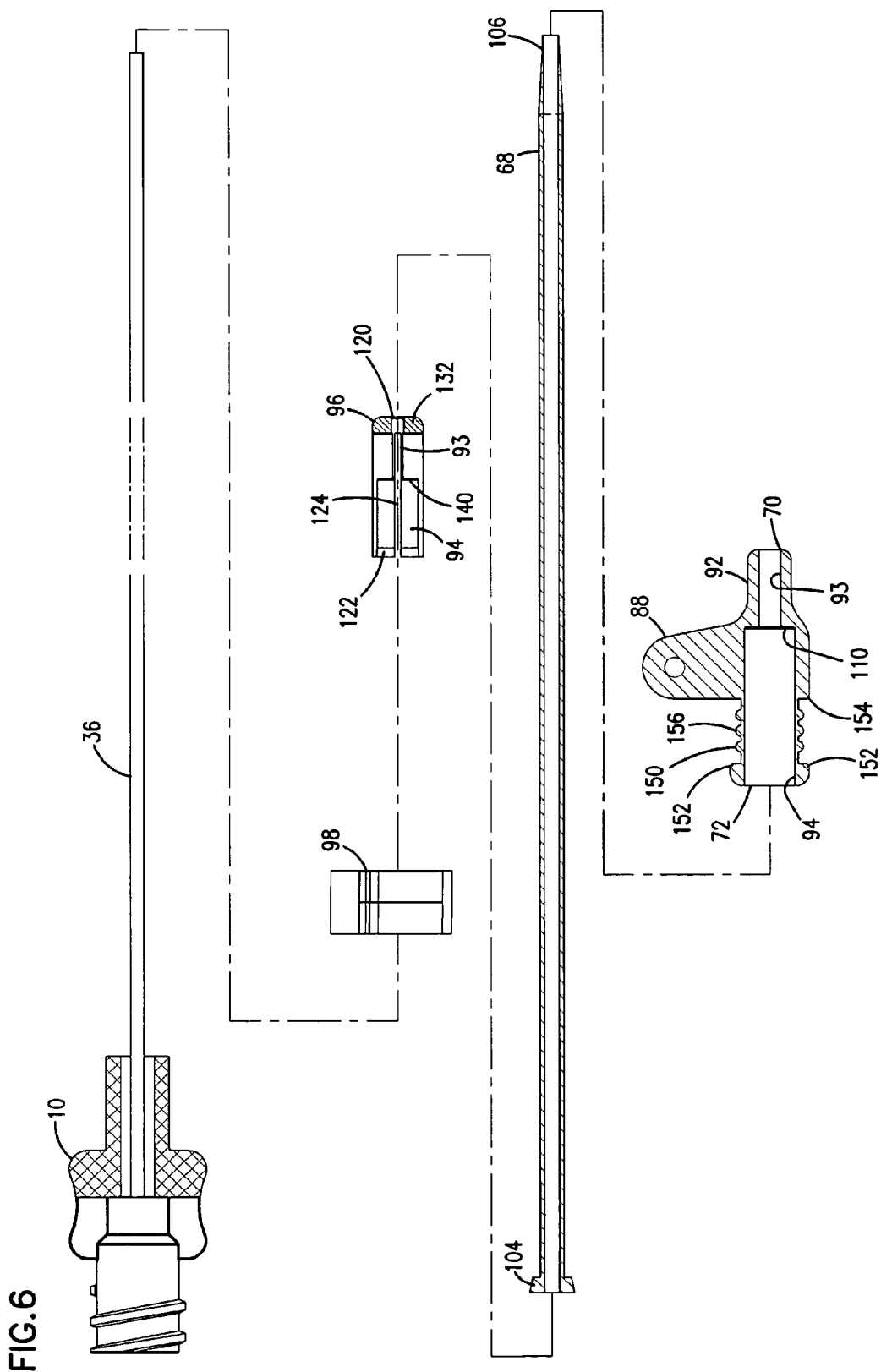
FIG. 6 is an exploded cross-sectional view of a drug delivery catheter and a connector of the delivery system of the present invention.
Figure 9:
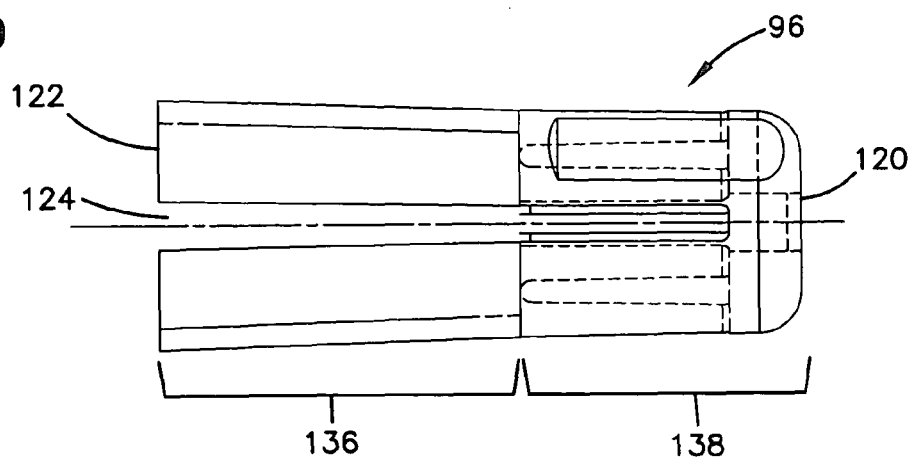
FIG. 9 is a side view of the collet of FIG. 7.
Figure 10:
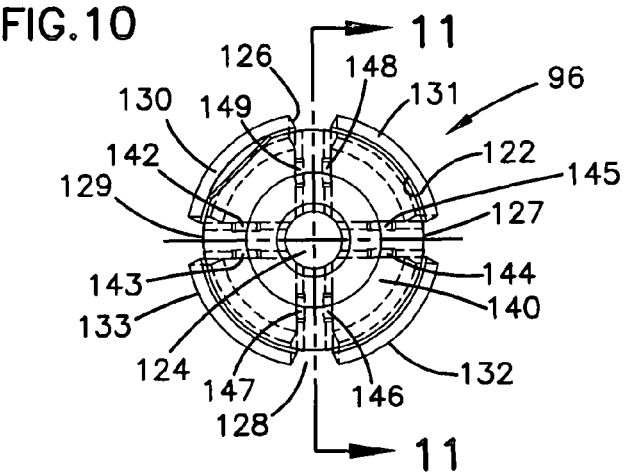
FIG. 10 is an end view of the collet of FIG. 7.
Figure 11:
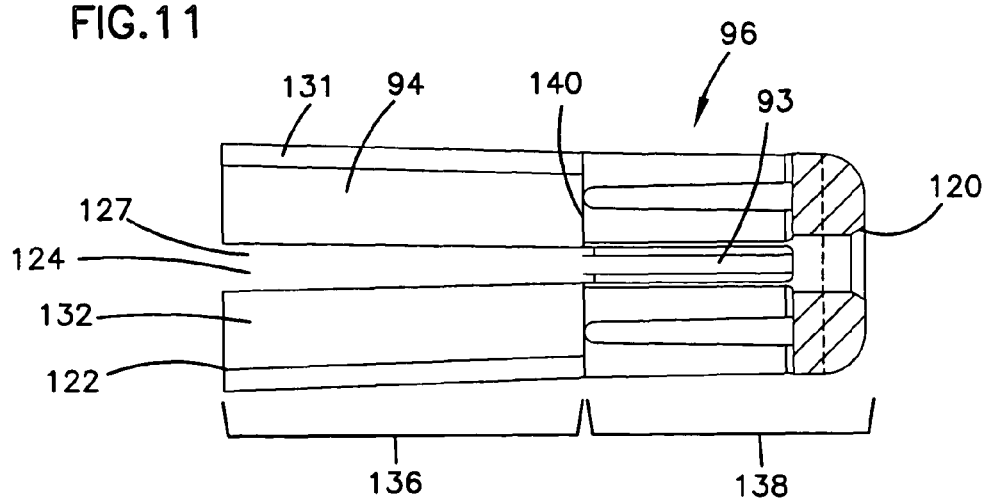
FIG. 11 is a cross-sectional view of the collet of FIG. 7, taken along line 11-11 of FIG. 10.

As shown in FIGS. 4-6, the connector 64 is assembled by inserting the sleeve 68 into the second opening 72 of the collar 92 so that it emerges from the first opening 70. The sleeve 68 includes a flared portion 104 at its proximal end and a tapered area 106 at its distal end. The sleeve 68 is sized to fit within the first chamber 93 of the collar 92. The flared portion 104 of the sleeve 68 is sized so that it will not fit within the first chamber 93 but will fit within the collet chamber 94. The flared portion 104 will contact the end wall 110 of the second chamber 94 to retain a portion of the sleeve 68 within the collar 92.

The sleeve 68 is configured to provide a larger outer diameter than the delivery catheter 36 to facilitate the healing of the wound in the vessel wall. Referring back to FIG. 1, the incision site 40 in the vessel wall is typically larger than the outer diameter of the delivery catheter 36. In many procedures, a larger diameter catheter is introduced through the incision site 40 for the purposes of mapping out the patient's vasculature using radiopaque material. After this mapping procedure is complete, the drug delivery catheter 36 is introduced through the incision site 40. The presence of the sleeve 68 surrounding the drug delivery catheter 36 at the incision site 40 facilitates healing of the vessel wall around the system. The sleeve may be made of polyurethane or many other types of materials. The outer diameter of the sleeve 68 is preferably at least about 0.04 inch or 1.0 mm, or at least about 0.06 inch or 1.5 mm or about 0.08 inch or 2 mm. The inner diameter of the sleeve 68 is configured to receive the drug delivery catheter 36.

The material of the sleeve 68 will be selected to be soft enough to bend easily as it is positioned at the incision site and not cause damage to the body lumen wall. In addition, the material of the sleeve should be rigid enough to allow the sleeve to be slid over the catheter. A material with a durometer in the range of 80 to 100 Shore A, or more specifically 90 to 95 Shore A may be used. In one embodiment, the durometer of the sleeve material is about 93 Shore A.

The length of the sleeve 68 may be at least about 1 inch, or more typically at least about 2 inches. The maximum length of the sleeve may be about 6 inches, or more typically about 5 inches. The sleeve 68 may have a length of about 4 inches in one embodiment. The sleeve 68 is configured to be long enough to extend from the connector 64 at a connection site to the incision site where the system penetrates a vessel wall. The sleeve length may vary depending on the particular application for the delivery system.

After the sleeve 68 is positioned within the collar 92, the collet 96 is inserted into the second chamber or collet chamber 94 of the body 92. The collet 96 will surround a portion 102 of both the tubing 60 and the delivery catheter 36, and the collet surrounds a portion 115 of the catheter 36 alone (FIG. 4).

FIGS. 7-11 further illustrate the collet structure. The collet includes a first opening 120, second opening 122 and a central passageway 124. The body of the collet is split along its sides at four different open areas extending from the second opening 122 along part of the length of the collet toward the first opening 120. These four open sections 126, 127, 128, 129 in between four panels 130, 131, 132, 133 allow the collet to be partially collapsed or constricted around the overlap area of the tubing 60 and the delivery catheter 36. The four panels 130, 131, 132, 133 extend from a ring portion 137 that encircles the central passageway 124. A portion 136 of the collet surrounds the first portion 102 of the overlap area 100 of the tubing 60 and the catheter 36. The collet also includes a portion 138 that surrounds the portion 115 (FIG. 4) of the delivery catheter 36 but does not surround the tubing 60. When the connection between the tubing 60 and the catheter 36 is made, the tubing 60 is pushed over the proximal end 99 (FIG. 4) of the delivery catheter 36 until the tubing contacts the inner wall 140 of the collet. The collet is a one-piece structure and is a more rigid piece than the collar 92, the drug delivery catheter 36 or the soft tubing 60.

In one embodiment, the collet 92 is formed from plastic or metal. In particular, the collet 92 may be made of DELRIN® acetal material. The thickness of the panels 130, 131, 132, 133 may be about 10-16 mils, or about 12-14 mils, at the proximal end of the collet, and become slightly thicker toward the distal end of the collet.

The collet allows the clamp to achieve better compression force on the overlap area of the tubing and the catheter and a better clamping force on the catheter alone in portion 115. The collet 96 helps to transmit the radially inward force of the clamp 98 to the tubing 60 and the catheter 36. The collet provides rigidity at the area of the connector where the clamp 98 applies a radially inward force to a portion of the overlap area. As a result, the collet limits the reduction of the inner diameter of the drug delivery catheter 36 that is caused by the clamping force. The collet therefore limits the collapsibility of the drug delivery catheter 36.

The structure of the collet 92 is best illustrated in the perspective views of FIGS. 7 and 8. The cross-section views of the collet 92, such as in FIG. 6, may give the impression that the collet is shorter than it actually is because of the open areas 126, 127, 128, 129. When positioned inside the cavity 94 of the sleeve 68, the collet 92 extends from the end wall 110 of the cavity 94 to the proximal end of the collar. The term collet 92 as it is used herein is defined as a band structure with an open area in the middle that may be made of any material that is more rigid than the materials of the tubing and the catheter.

In the section 136 of the collet 92 that surrounds only the catheter 36, positive stop structures may be included on the walls of the panels 130, 131, 132, 133. For example, as shown in FIG. 8, positive stop structures 142, 143 are located on the sidewalls of panels 130, 133, respectively. These positive stop structures 142, 143 establish a minimum distance between the panels 130, 133. During radial compression of the collet, the section 136 will radially compress until the stop structures engage each other. Positive stop structures 144, 145 are located on the sidewalls of panels 131, 132, respectively. Additional positive stop structures 146, 147, 148, 149, shown in FIG. 10, limit the distance between the panels 130, 131, 132, 133 in the section 136 of the collet 92. These eight positive stop structures ensure that despite the compression of the catheter 36 by the clamp, the inner lumen of the catheter will not collapse. In alternative embodiments, the positive stop structures may have a different shape or may interlock in some way.

Again referring to the exploded view of FIG. 6, after the collet 96 is positioned within the collet cavity 94 of the collar 92, the clamp 98 is positioned around a clamp band area 150 of the collar 92. The clamp band area 150 of the collar 92 is a recessed area defined between a first ridge 152 and a second ridge 154. The ridges 152, 154 help bound the clamp 98 within the clamp band area 150 when the clamp 98 is in its open position before it is moved to its closed position. The surface of the clamp band area 150 may include bumps 156 to facilitate transmitting the force of the clamp 98 to the tubing 60 and the catheter 36. These bumps are illustrated in the collar 92 shown in FIGS. 2, 4 and 6. These bumps are not required however, and the clamp band area 150 is shown without the bumps 156 in FIGS. 5 and 14-16.

Now referring to FIGS. 12-18, the clamp 98 includes an upper jaw 160 spaced from a lower jaw 162. A tongue 164 is configured to fit within the jaws 160, 162. Teeth 166 on the tongue 164 will interlock with teeth 168 on the lower jaw 162. When the tongue 164 is inserted between the jaws 160, 162, the clamp 98 provides a radially inward force upon the tubing 60 surrounding the delivery catheter 36.

Figure 15:
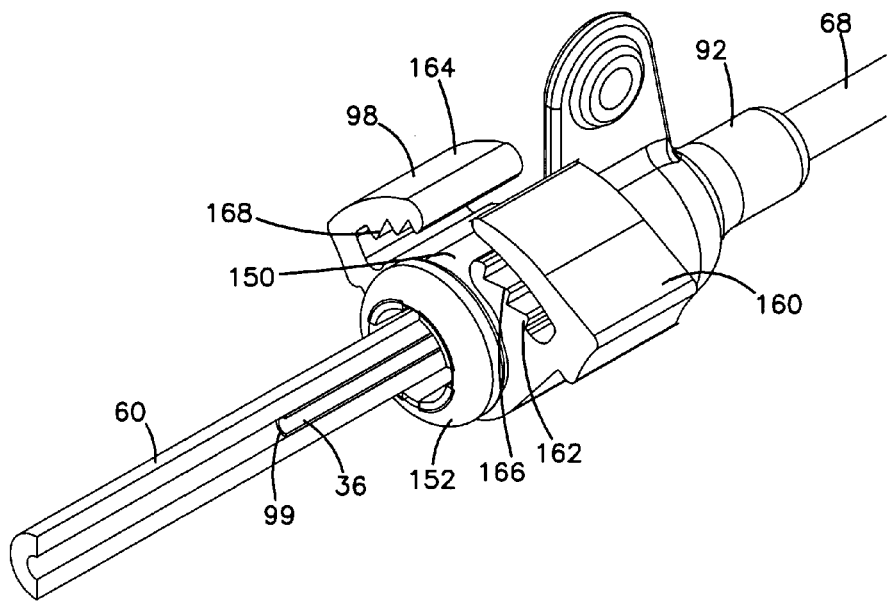
FIG. 15 is a perspective view of the connector of FIG. 12 in an open position.
Figure 16:
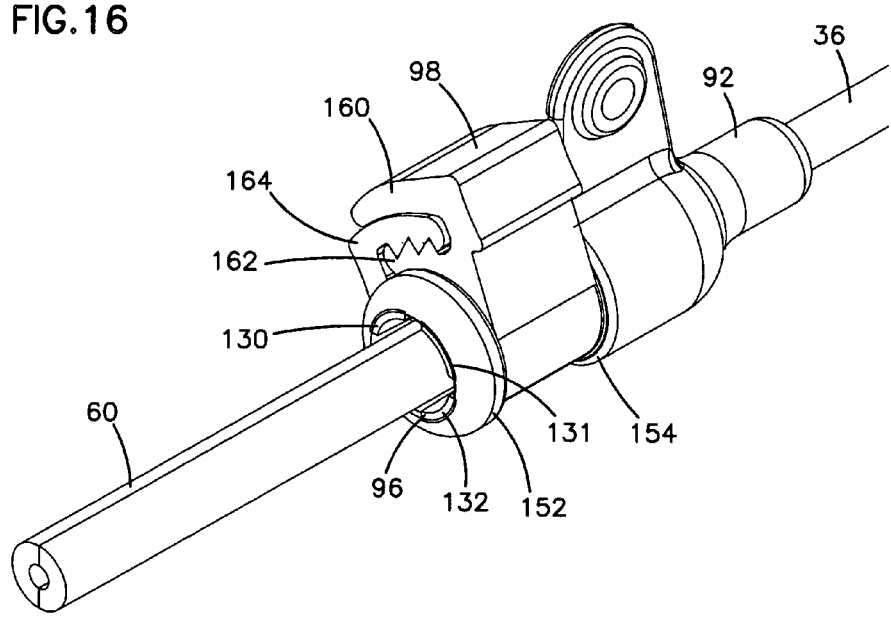
FIG. 16 is a perspective view of the connector of FIG. 12 in a closed position.
Figure 17:
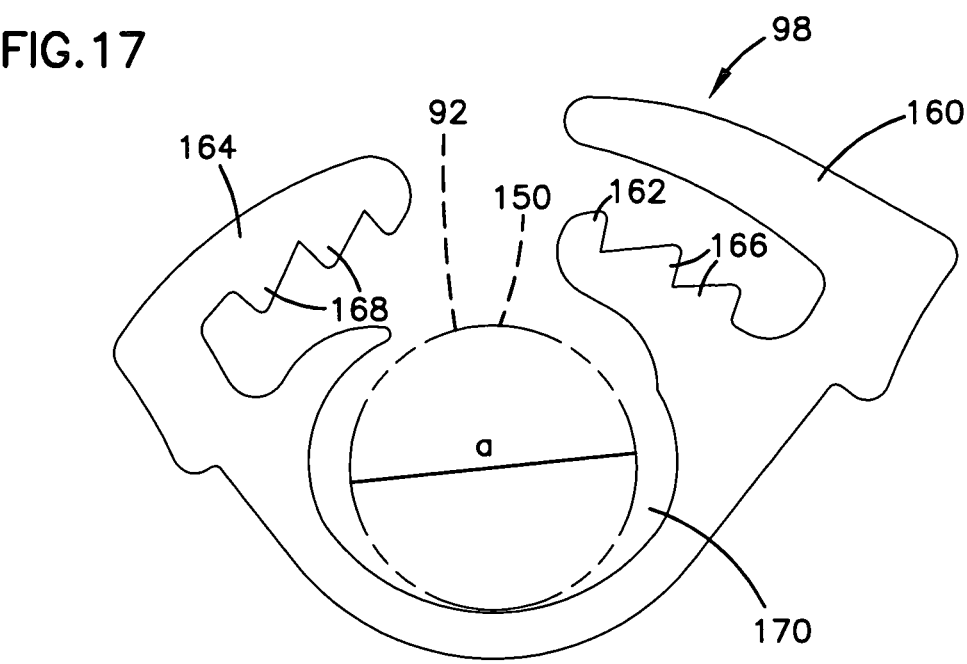
FIG. 17 is an end view of a clamp included in the connector of FIG. 12 in an open position.
Figure 18:
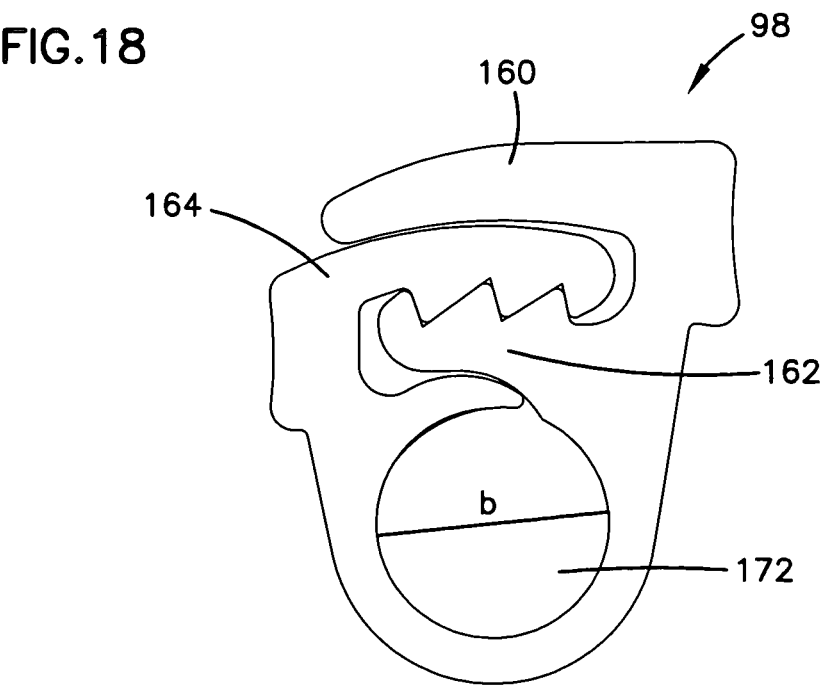
FIG. 18 is an end view of the clamp of FIG. 17 in a closed position.

The lockable clamp 98 is in an open position when it is positioned on the collar 92 and when the tubing is inserted into the collet cavity 94. This open position is illustrated in FIGS. 15 and 17. The jaws 160, 162 and tongue 164 are squeezed together so that the teeth interlock and close the clamp. Squeezing the clamp into the closed position makes the connection between the tubing and the catheter. The closed or locked position of the clamp 94 is illustrated in FIGS. 16 and 18. In one embodiment of the connector, the clamp cannot be unlocked once the teeth have interlocked to close the clamp. The clamp is made of a material that is more rigid than the collar. In one embodiment, the clamp is made of plastic or metal. In one embodiment, the clamp 98 is made of a Delrin® acetal material. Many other materials are possible for the clamp 98.

In its open position shown in FIG. 17, the clamp 98 defines an open area 170. The clamp band area 150 of the collar 92 will be positioned in this open area 170 of the clamp 98. When the clamp is in the open position, the collar 92 will have a diameter a shown in FIG. 17. When the clamp 98 is moved into the closed position as shown in FIG. 18, the clamp 98 will apply a radially inward force to the collar 92 at the clamp band area 150. In this closed position, the clamp 98 encircles a smaller area 172 that has a diameter b that is smaller than the diameter a of the clamp band area 150 of the collar 92, as shown in FIG. 18.

In one embodiment, the clamp has three interlocking teeth 166 on the tongue 164 and three interlocking teeth 168 on the lower jaw 162. The clamp may be provided with many different numbers of teeth and configurations of teeth, such as two teeth on each structure, or four teeth. In one embodiment, the tension needed to move the clamp into the locking position is best accomplished with the assistance of a tool such as a forceps. In this embodiment, it is possible to use ones fingers to partially close the clamp so the two of the three teeth on each structure are engaged, but to engage the third set of teeth, a tool that can apply more leverage will be used to move the clamp into its final closed position.

In one embodiment, catheter 36 includes two or more areas of different stiffness along its length. In one embodiment, the most distal section of the catheter near the delivery tip 42 is less rigid than the remainder of the catheter. A less rigid tip may prevent damage to the vessel wall where the delivery tip 42 is located.

In one embodiment, the catheter may have three sections of different rigidity. The tip region may be the most flexible, while the most proximal section may be the most rigid. In between, a transition segment may have a rigidity in between that of the tip section and the most proximal section.

The catheter in one embodiment may include three different layers. An inner layer provides sufficient lubricity along the inner surface of the catheter so that a guide wire will slide easily with respect to the catheter. The use of a guide wire with the delivery catheter will be discussed further in the context of how the catheter is positioned in the body. The inner layer may be a polymer, such as a vinyl polymer. In one embodiment, the inner layer is polytetrafluoroethylene, or PTFE, such as TEFLON® material. In one embodiment, the inner layer is at least about 0.5-mil thick, or about 1 mil.

A middle layer provides strength, columnar stiffness, pushability and resistance to elongation. The middle layer can be a metal material, such as a braided metal wire. In one embodiment, the middle layer is a braid of 3-mil stainless steel wire. In one embodiment, the wire has a flattened shape with dimensions of 3 mil by 0.5 mil.

The outer layer serves to enclose the remainder of the catheter with a biocompatible material that will easily travel through the body's vasculature and tissue. In one embodiment, the outer layer is a polymer material, such as polyether block amide. The outer layer may be at least about 1 mil thick, or may be about 3 mil thick. For example, the outer layer may be PEBAX® material with a thickness of about 3 mil. In one embodiment, the outer layer has varying stiffness along the length of the catheter, thereby providing varying segments of stiffness to the catheter. In an alternative embodiment, the middle layer may be a stainless steel braid with areas of different density along the length of the catheter to provide the catheter with segments of different stiffness.

Figure 19:
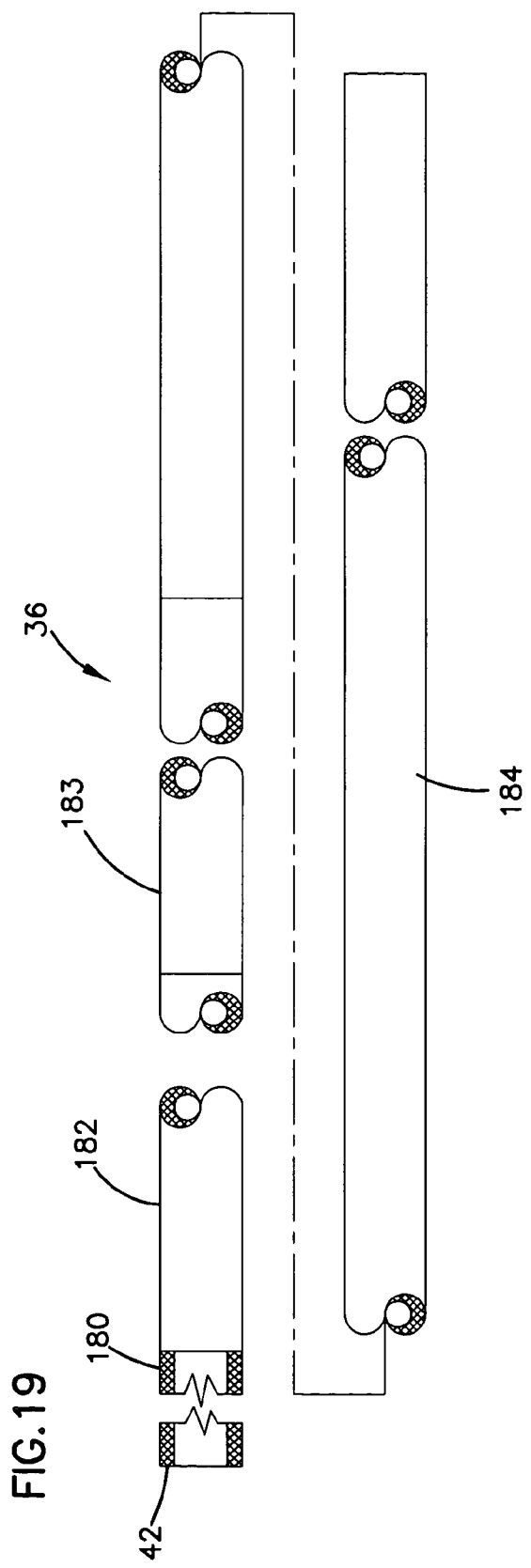
FIG. 19 is a side view of a drug delivery catheter of the present invention.
Figure 20:
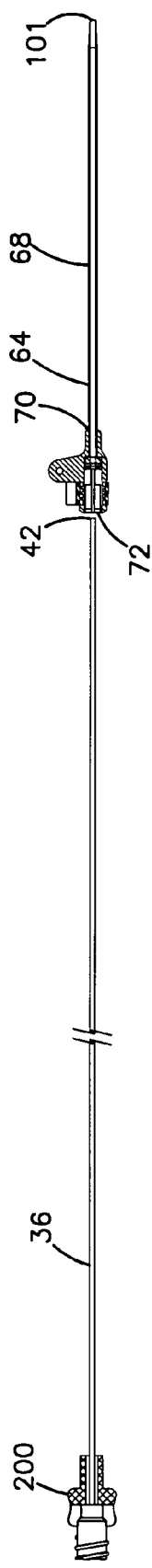
FIGS. 20-22 show steps of using a drug delivery catheter and connector of the present invention.
Figure 21:
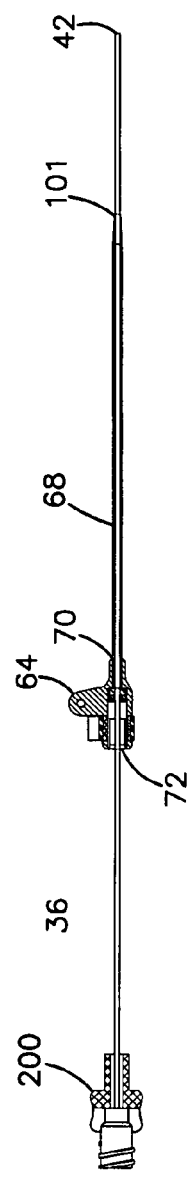

One embodiment of a delivery catheter 36 is illustrated in FIG. 19. At its tip 42, the catheter 36 includes radiopaque marker 180. The marker 180 may be at least about 0.05 inches long, or, more specifically at least about 0.07 inches long. In one embodiment, the marker 180 is at least about 0.10 inches long. Immediately adjacent the marker 180, the distal section 182 is the most flexible portion of the catheter 36. This distal section 182 may be about 1 to 5 inches in length, or, more specifically, about 2 to 4 inches in length. In one embodiment, the distal section is about 3 inches in length. A transition section 183 is more rigid than the distal section 182 but more flexible than the proximal section 184. In the distal section 182, the outer layer may have a durometer of about 30-40 Shore D, or 35 Shore D. In the transition section 183, the outer layer may have a durometer of about 50-60 Shore D, or 55 Shore D. In the most proximal section 184, the outer layer may have a durometer of about 65-75 Shore D, or 72 Shore D.

The catheter is structured to enable pushability along a guide wire and allow the catheter to track sharp direction changes in the guide wire. The more rigid nature of the proximal and transition sections accomplish these goals. The most distal section 182 with increased flexibility reduces damage to the vessel wall when the catheter 36 is positioned within a body lumen and results in better stability of the catheter tip location. The outer diameter of the catheter will vary for different applications. In one embodiment, the catheter outer diameter is no larger than about 0.06 inch or 1.5 mm, or about 0.04 inch or 1 mm. The catheter 36 may have a colored appearance on its outer surface so that it may be more easily viewed within the tubing at the overlap area 100.

The steps of using the delivery system of the present invention to deliver a fluid to an area of a body will now be described with reference to FIGS. 2, 6 and 20-22. An important application of this system is its use in delivering drugs, such as disease treatments, to an area of the body. However, this same system could be used to deliver other fluids or withdraw fluids from the body. Although the method of using the system for delivery of agents will be described in detail, these same steps could apply to the process of withdrawing fluid from the body using the system. This system can be used in arterial system of a body, especially in the context of disease treatment. However, the system can also be used in the veinous system for either delivery or withdrawal of fluids.

FIG. 6 shows an exploded view of the delivery catheter 36 and the components of the connector 64. To assemble the connector, the sleeve 68 is inserted into the collar 92. Next, the collet 96 is inserted into the cavity 94 of the collar 92. Finally, the clamp band 98 is placed over the clamp band area 150 on the collar. The clamp band 98 is in the open position. These assembly steps result in the connector 64 shown in FIGS. 12-15.

The connector 64 may be already positioned on the catheter 36 when the system is provided to surgeons. In one method of positioning the connector on the catheter, the proximal end of the catheter is inserted into the distal end of the connector 101, until it emerges from the proximal end of the connector 64. Then the Luer housing 200 is attached to the proximal end of the catheter.

During drug delivery procedures such as regional chemotherapy, the tip 42 of the drug delivery catheter is positioned at a location in the liver, for example, and chemotherapy is delivered to that location for a period of time by injecting fluid agents into the access device 34. The first step in accomplishing this procedure is to map out the vasculature of the liver to determine the best placement location of the tip of the drug delivery catheter. This mapping process is done using a mapping catheter and injecting radiopaque dye into the area. The mapping catheter is introduced into the body, such as at the femoral or subclavian locations shown in FIG. 1. The mapping catheter is positioned so that its tip is in the liver area. After repeated injection of radiopaque dye and image observation, the desired location of the drug delivery catheter is determined.

Next, a guide wire is inserted into the lumen of the mapping catheter if a guide wire is not already present. A sheath structure typically surrounds the mapping catheter. The mapping catheter is withdrawn leaving the guide wire and sheath structure in place. The distal end of the drug delivery catheter receives the proximal end of the guide wire and the drug delivery catheter is fed along the length of the guide wire until the tip of the delivery catheter is positioned in the desired location. Next, the guide wire is removed and the sheath structure is removed by splitting it along a seam and pulling it out of the patient's body.

Figure 22:
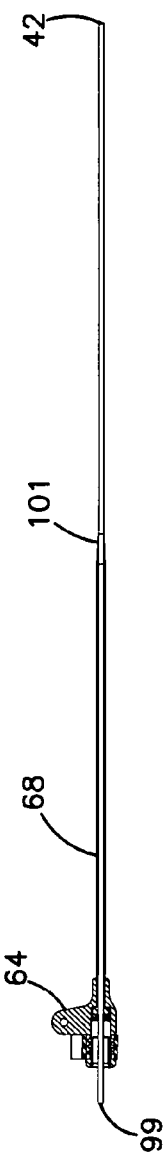

As the end of the sheath structure is removed through the incision site in the body lumen, the sleeve 68 of the connector is slid into position within the incision site in the body lumen. The outer diameter of the sheath and the outer diameter of the sleeve 68 are typically about the same, to reduce bleeding and speed healing of the incision site in the body lumen. Then the catheter is cut so that just a portion of it extends proximally from the connector, thereby removing the Luer housing 200, as shown in FIG. 22. In one embodiment, the catheter is cut so that at least about 0.5 cm of the catheter extends from the connector, providing sufficient catheter length outside of the connector cavity 94 to insert the catheter into the tubing. More particularly, the catheter is cut so that at least about 1 cm extends from the connector.

Next, the tubing 60 is put in position over the cut proximal end 99 of the drug delivery catheter 36. As the tubing is slid over the end of the catheter, the catheter location can be stabilized, for example by grasping the catheter through the sleeve 68. After this step, the distal end 224 of the tubing 60 is positioned within the cavity 94 of the connector 64, abutting the wall 140 of the collet 96. Where the tubing 64 has at least partially clear walls, the position of the catheter within the tubing can be visually verified. A colored surface of the catheter can assist with this visual inspection.

The clamp 98 is then moved into its closed position, thereby applying force on a portion 102 of the overlap area 100 between the tubing 60 and the catheter 36. The connector may be secured to tissue using the suture hole 90, but this step is optional. Tubing 60 is tunneled subcutaneously from the location of the connector 64 to the desired location of the access device 34. The access device 34 is implanted subcutaneously and secured to the patient's tissue. The tubing 60 is cut to the appropriate size and connected to the outlet tube 82 of the port 34.

From time to time, the tip location of the drug delivery catheter will be modified to deliver chemotherapy to a different part of the liver. When this repositioning is needed, the physician can access the connector 64 subcutaneously and cut the soft tubing adjacent the connector. Then a guide wire may be inserted into the lumen of the catheter 36 to assist with sliding a new catheter with a connector 64 over the guide wire after removing the previous catheter. The new catheter is then connected to the tubing as previously discussed.

The above specification, examples and data provide a complete description of the manufacture and use of the composition of the invention. Since many embodiments of the invention can be made without departing from the spirit and scope of the invention, the invention resides in the claims hereinafter appended.

We claim:

1. An implantable system for delivering fluid to a body including:
   a flexible first catheter;
   a flexible second catheter having an inner diameter sized to receive the first catheter, where one end of the first catheter is configured to be received within one end of the second catheter, wherein when the first and second catheters are connected, a portion of the first catheter is fitted within a portion of the second catheter to form an overlap area wherein each of the first and second catheters have constant wall thickness in the overlap area;
   a collar with a first opening configured to encircle the first catheter and a second opening configured to encircle the second catheter, wherein the first opening is smaller than the second opening, wherein the collar is configured to surround at least a first portion of the overlap area of the first and second catheters; and
   a clamp for applying a radially inward force to at least the portion of the collar that surrounds the overlap area to hold the first and second catheters together.

2. The system of claim 1 further comprising an access device configured to establish fluid communication with the second catheter, the access device comprising:
   a reservoir having an open top and a closed bottom,
   a pierceable and resealable septum received in the open top, and an outlet tube in fluid communication with the reservoir, wherein the outlet tube is configured to be received within one end of the second catheter.

3. The system of claim 1 wherein the clamp moves between a first open position and a second locked position, wherein in the open position the clamp can receive an end of the second catheter and wherein in the closed position the clamp applies the radially inward force to the overlap area, wherein the clamp locks into the closed position.

4. The system of claim 3 wherein the clamp includes interlocking teeth that maintain the clamp in the closed position.

5. The system of claim 1 wherein the clamp comprises:
   a pair of spaced jaws including a first jaw and a second jaw, the first jaw including teeth; and
   a tongue configured to be inserted between the spaced jaws when the clamp is in the closed position, the tongue including teeth to mesh with the teeth on the first jaw.

6. The system of claim 1 wherein the collar includes a recessed area for receiving the clamp.

7. The system of claim 1 wherein the collar defines a distal cavity adjacent to the first opening and a proximal cavity adjacent to the second opening, wherein the distal and proximal cavities are cylindrical cavities, wherein the distal hollow cavity has a diameter smaller than a diameter of the proximal cavity.

8. The system of claim 1 wherein the collar defines a proximal cavity adjacent to the second opening and encircled by the clamp, wherein the first portion of the overlap area is positioned within the proximal cavity, the connector further comprising a collet within the proximal cavity, wherein the collet is configured to surround at least the first portion of the overlap area of the first and second catheter, wherein the collet is more rigid than both the first and second catheters, wherein the collet further surrounds a portion of the first catheter that does not overlap with the second catheter.

9. The system of claim 8, wherein the collet comprises: a ring portion encircling an open passage; and
four panels extending from the ring portion, the four panels defining four open areas between the four panels.

10. The system of claim 9, wherein the first and second openings of the collar are axially aligned.

11. The system of claim 10 further comprising a sleeve extending from the first opening, wherein the sleeve is configured to surround the first catheter for a sleeved portion of the first catheter, wherein the sleeve has an outer diameter larger than an outer diameter of the first catheter.

12. The system of claim 11 wherein the sleeved portion is about two to six inches long.

13. The system of claim 11 wherein the sleeve outer diameter is at least about 50% larger than the first catheter outer diameter.

14. The system of claim 13 wherein the sleeve outer diameter is at least about twice as large as the first catheter outer diameter.

15. The system of claim 11 wherein the sleeve includes a flared lip portion at one end, wherein the lip portion is configured to engage an end wall of the proximal cavity within the collar.

16. The system of claim 1 further comprising a sleeve extending from the first opening, wherein the sleeve is configured to surround the first catheter for a sleeved portion of the first catheter, wherein the sleeve has an outer diameter larger than an outer diameter of the first catheter.

17. The system of claim 16 wherein the sleeved portion is about two to six inches long.

18. The system of claim 17 wherein the sleeve outer diameter is at least about 50% larger than the first catheter outer diameter.

19. The system of claim 18 wherein the sleeve outer diameter is at least about twice as large as the first catheter outer diameter.

20. The system of claim 16 wherein the sleeve includes a flared lip portion at one end, wherein the lip portion is configured to engage an end wall of the proximal cavity within the collar.

* * * * *